United States Patent [19]
Florin

[11] 4,348,562
[45] * Sep. 7, 1982

[54] POSITION SENSITIVE MERCURY SWITCH

[76] Inventor: Robert E. Florin, 7921 S. Painter Ave., Whittier, Calif. 90602

[*] Notice: The portion of the term of this patent subsequent to Aug. 4, 1998, has been disclaimed.

[21] Appl. No.: 226,367

[22] Filed: Jan. 19, 1981

Related U.S. Application Data

[63] Continuation-in-part of Ser. No. 133,002, Mar. 24, 1980, Pat. No. 4,282,412, which is a continuation-in-part of Ser. No. 935,363, Aug. 21, 1978, abandoned.

[51] Int. Cl.³ .............................................. H01H 29/20
[52] U.S. Cl. ............................... 200/52 R; 200/61.52; 200/220
[58] Field of Search ............ 200/52 R, DIG. 2, 61.47, 200/61.52, 220, 221, 228, 229, 236

[56] References Cited
U.S. PATENT DOCUMENTS
4,282,412  8/1981  Florin ................................ 200/52 R Primary Examiner—James R. Scott
Attorney, Agent, or Firm—Lyon & Lyon

[57] ABSTRACT

A mercury switch assembly is adapted to be secured to an anterior horizontal surface of a patient and connected to an electrical alarm system. The switch assembly comprises a head chamber and a foot chamber connected by a throat passageway. A ball of mercury moves from the head chamber through the throat passageway and into the foot chamber to complete an electrical circuit when the switch assembly is tilted from horizontal by a predetermined degree of inclination. The head chamber is generally elliptical with lateral extensions. The throat passageway is narrow and shallow. The foot chamber is deep and rounded. The ball of mercury normally lies within the head chamber in the horizontal position, but establishes electrical connection between a novel form of terminals contained in the foot chamber when the tilt threshold of the switch assembly is reached. The foot chamber retains the mercury ball in contact with the terminals despite subsequent movements of the switch assembly until the switch assembly is removed from the patient and inverted to place the foot chamber vertically above the head chamber thereby causing the ball of mercury to return by gravity to the head chamber. Critical ranges of dimensions and angles of interior surfaces are provided.

12 Claims, 4 Drawing Figures

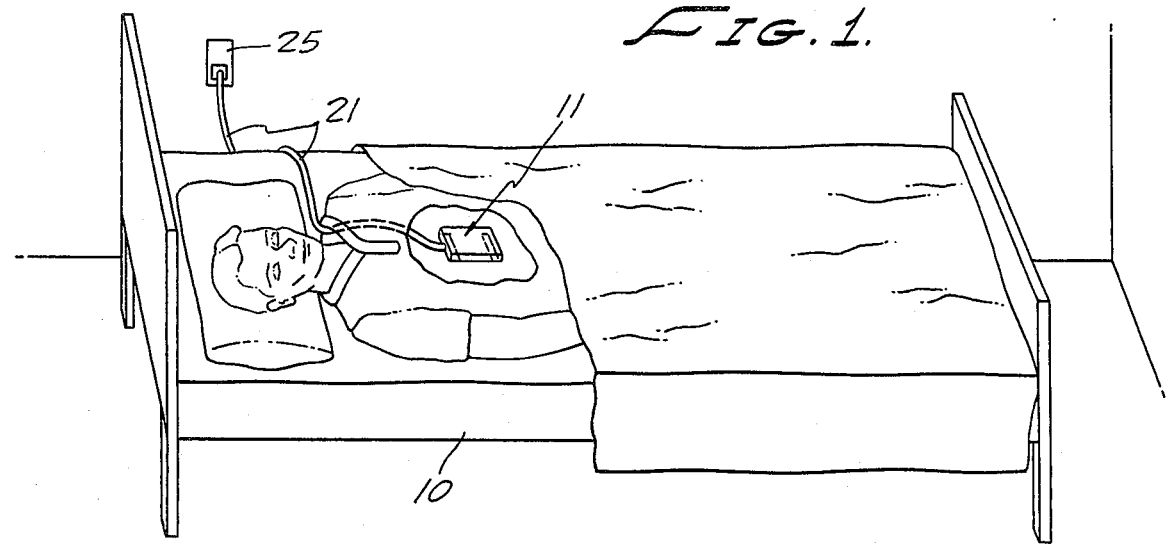
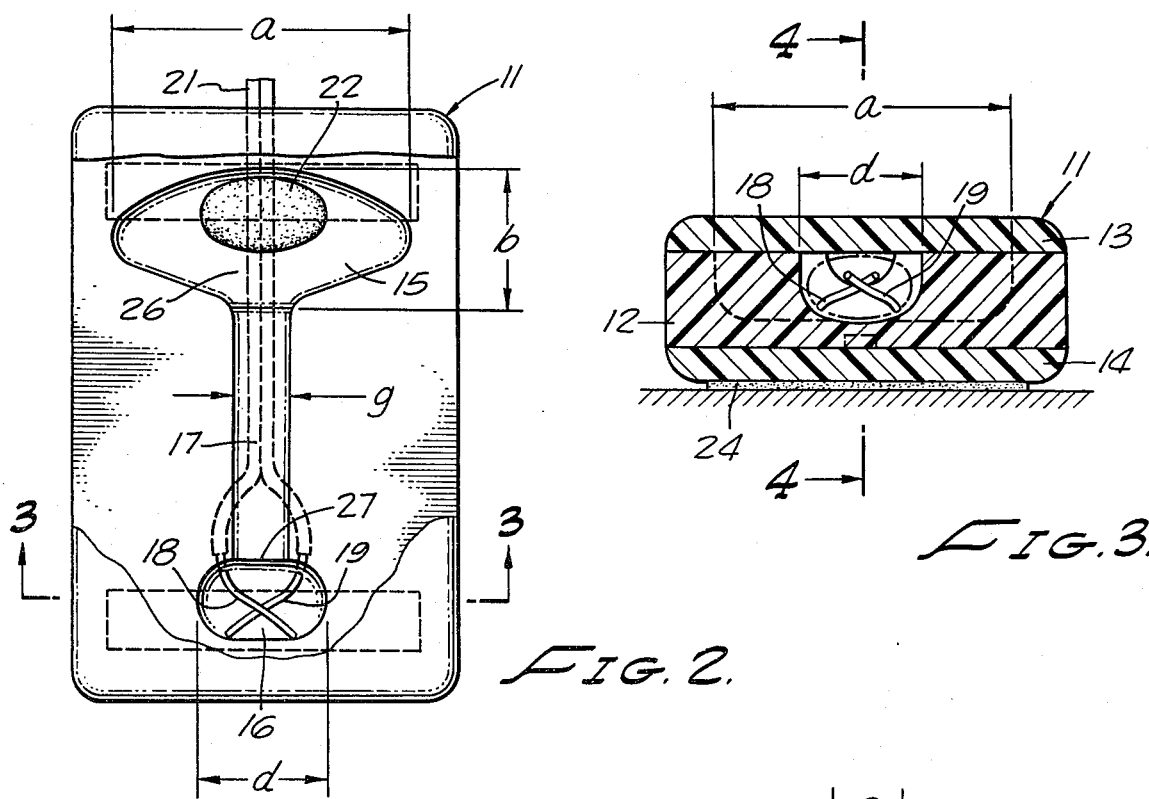
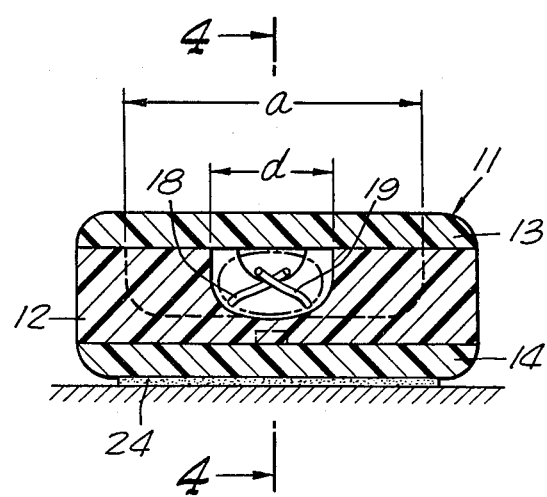
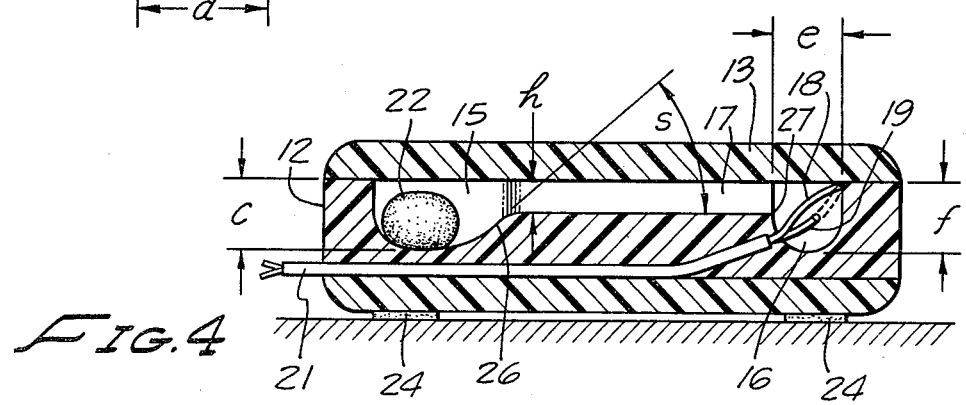

POSITION SENSITIVE MERCURY SWITCH

CROSS-REFERENCES TO RELATED APPLICATIONS

This application is a continuation-in-part of applicant's pending application Ser. No. 133,002 filed Mar. 24, 1980, now U.S. Pat. No. 4,282,412 granted Aug. 4, 1981. Ser. No. 133,002 was a continuation-in-part of Ser. No. 935,363 filed Aug. 21, 1978, now abandoned.

BACKGROUND OF THE INVENTION

This invention relates to an alarm switch having utility in the field of medicine and nursing which affords a reliable means of detecting certain specific angular deviations of a surface of a patient's body with respect to the horizontal or supine position. The particular utility of such a position-sensitive alarm switch lies in its ability to forewarn attendant personnel of certain movements of a monitored patient that may precede a fall.

In the past, various restraining or confining devices such as fabric jackets attached to the bed, side rails, and limb restraints have been employed with varying success. Rather frequently, confused or sedated patients manage to escape such restraints, and they sometimes fall to the floor when attempting to get out of bed or after leaving the bed while walking about the room. The incidence of significant injury from such accidents is substantial, and, despite special efforts by personnel attending such patients, injuries continue to occur.

Known devices and prior systems have not been designed to selectively signal the specific changes in patient position encompassed by the present invention without causing frequent false alarms. Also, the prior art relating to the use of position-sensitive switch devices to operate an alarm system have not been readily adaptable to monitoring of patients seated in chairs or wheel chairs as well as bed patients.

SUMMARY OF THE INVENTION

An important objective of the present invention is to provide an alarm device that is selective in operation and is capable in detecting certain specific movements of a patient's body that occur reliably before fall from bed or a chair, i.e., a change from an approximate horizontal position of an anterior surface of the patient's chest or thigh to a more vertical position of either of these surfaces which may be monitored. It has been determined that switch operation at 40° to 70° of elevation of the monitored surface, and preferably from 50° to 60°, provides reliable warning of the change in position of the patient that may precede a fall without generating unnecessary false alarms associated with random changes or adjustments of the patient's resting position. Activation of an alarm system when the patient does exceed the switch threshold alerts the personnel attending the patient to the possibility of impending injury and may prevent such an occurrence.

Another object of the invention is to provide an alarm system capable of detecting certain changes of position of the monitored patient which will continue to operate even if the patient changes position from that which activated the alarm, and will continue until deactivated by the nursing staff. This also has value in cases where absolute bed rest is required, and alerts the nursing staff to such patients who may be more active than desirable.

Another object of the invention is to provide an alarm system which will integrate with existing hospital call systems and activate an individual patient's call light and/or buzzer, thereby notifying the nurse of the exact location of the patient at risk from excessive activity. A system capable of identifying each patient so monitored permits simultaneous monitoring of a number of patients in a nursing ward or special care unit, indicating abnormal activity in one or more of those patients simultaneously. When integrated in such a fashion, the invention required no additional power or electrical devices. In situations where no existing call or alarm system is available, a separately powered alarm system may be connected to provide audible or visual notice of excessive motion by the patient.

Another object of this invention is to provide a novel configuration of the electrodes in the foot chamber which insures reliable contact with the ball of mercury.

Other related objects of this invention are the provision of a simple switching device and the associated electrical circuitry which is fully automatic in operation after application to the patient, and is dustproof, waterproof, and requires no adjustment or service after proper application.

A preferred embodiment of the invention includes a rectangular enclosure with parallel non-conductive surfaces, containing a cavity resembling a longitudinal half section of a bar-bell, flat on the upper surface and convex on the interior aspect. The cavity is sealed within the non-conductive surfaces and contains a small amount of mercury. The longitudinal axis of the cavity is aligned with both the long axis of the enclosure and the long or spinal axis of the patient. Two chambers of unequal size are connected at each end of a middle axial portion of the cavity which is narrow and acts as a passageway for the mercury. The larger head chamber is rounded or elliptical in outline, extends laterally in both directions, and is deeper than the throat passageway. This configuration allows for turning movements around the long axis of the assembly without inappropriate activation of the switch device and generation of false alarms. The junction between the head chamber and the throat passageway is smooth and tapered and acts to restrain the movement of the contained mercury ball in the head chamber from entering the throat passageway until a predetermined degree of inclination of the long axis of the assembly is reached. The throat passageway is uniform in its cross section, approximately semi-circular and connected to the smaller foot chamber which is roughly globular and is of a size designed to be substantially filled by the mercury ball and the contained electrodes when the switch assembly is in the operative or alarm position. The junction between the floor of the throat passageway and the foot chamber is sharp and angular, approximating 90°. This provides a dropoff into the relatively deep well-like reservoir in the foot chamber which acts to retain the mercury ball even during subsequent random displacements of the device after activation, which assures continuous operation of the alarm system connected to the contained electrodes once the switch has been actuated.

Other and more detailed objects and advantages will appear hereinafter.

BRIEF DESCRIPTION OF THE DRAWING

In the drawings:

FIG. 1 is a perspective view partly broken away, showing a preferred embodiment of this invention as applied to a bed patient.

FIG. 2 is a front view partly broken away, showing details of the switch assembly.

FIG. 3 is a transverse sectional view taken substantially on the lines 3—3 as shown in FIG. 2.

FIG. 4 is a sectional elevation taken substantially on the lines 4—4 as shown in FIG. 3.

DESCRIPTION OF THE PREFERRED EMBODIMENTS

Referring to the drawings, the bed is a standard hospital bed of the type used in hosptials, convalescent homes, etc. The bed 10 would normally be provided with retractable railings or fences, but these are omitted for clarity of illustration.

The switch assembly generally designated 11 has a rectangular body 12 closed by a cover plate 13 and a bottom plate 14. The body 12 and plates 13 and 14 may be formed of electrically non-conducting plastic material fixed together by conventional sealants. Alternatively, the internal surfaces only may be electrically non-conductive. Defined between the body 12 and the cover plate 13 are a head chamber 15 and a foot chamber 16 connected by a narrow passageway 17. Two metallic electrodes or terminals 18 and 19 extending from the two-wire cable 21 are spaced apart within the foot chamber 16 and are curved about the midline axis of the foot chamber. An electrically conducting liquid such as a ball of mercury 22 normally rests in the relatively wide head chamber 15, but when the switch assembly 11 is moved from horizontal position toward a vertical position beyond a 40° to 70° inclination, the mercury ball 22 moves down the throat passageway 17 and into the foot chamber 16 to establish an electrical connection between the terminals 18 and 19, where the curved electrodes insure reliable contact with the mercury ball, even under lateral turning movement. The head chamber 15 and the foot chamber 16 are each deeper than the narrow passageway 17. The cover plate 13 is flat on its underside and forms the roof of the head chamber 15, narrow passageway 17 and foot chamber 16. The surface 26 connecting the head chamber 15 to the narrow passageway 17 is smooth and rounded while the surface 27 connecting the narrow passageway 17 to the foot chamber 16 is sharp and abrupt.

Tests have shown that the optimum size of the ball of mercury is 3.5 mm. With regard to the head chamber 15, the width "a" should be 10 mm–20 mm, the height "b" should be 5.0 mm–10.0 mm, and the depth "c" should be 3.5 mm–5.0 mm.

With regard to the foot chamber 16, the width "d" should be 3.0 mm–7.0 mm, the height "e" should be 3.5 mm–5.0 mm, and the depth "f" should be 3.5 mm–5.0 mm.

With regard to the throat passageway 17, the width "g" should be 3.0 mm–4.0 mm, the depth "h" should be 2 mm–3.5 mm.

The slope "s" of the surface 26 in the head chamber 15 may be from 40°–70° inclination with respect to the bottom surface of the throat passageway 17, and the optimum range is between 50° and 60°.

In FIG. 4, the switch assembly is oriented in a horizontal position without lateral rotation about the long axis such as when applied to a patient's chest or thigh for monitoring, and the mercury ball 22 lies at the head chamber 15. Due to the particular design of the head chamber 15 with its lateral extensions and deeper floor, the mercury ball is retained in the head chamber during lateral rotations, and even during inclination of the throat passgeway 17 up to 40°–70°. Beyond that elevation, the mercury ball 22 enters the throat passageway 17 and rapidly moves down that passageway into the foot chamber 16, where the mercury submerges the contained electrodes 18 and 19 and establishes an electrical connnection between them, which in turn activates the external alarm system in a manner not shown. The effect of the particular design of the foot chamber 16 and the well-like effect of the sharp junction 27 upon the mercury ball present in the foot chamber 19, acts to retain the mercury ball within the foot chamber and in contact with type electrodes 18 and 19 in the manner of a latching relay. Only when the switch assembly is inverted to a 90° head-down position does the mercury ball move back through the throat passageway 17 and re-enter the head chamber 15, thus resetting the switch device for its next operational cycle.

Construction of the switch assembly 11 may be accomplished rather simply by fashioning the chambers 15 and 16 and the connecting passageway 17 within the upper surface of a block of solid plastic or similar insulating material 12. Small holes are drilled so as to enter the deep portion of the foot chamber 16 and the electrode wires introduced through such holes as to be exposed within the foot chamber 16, as is shown in FIG. 4. The several wires comprising the insulated cord 21 which connects the electrodes to the alarm system are brought out beneath the throat passageway and head chamber 15 in order to provide a secure anchor for the cord 21 and to guide the cord in the direction of the upper portion of the patient's body which is common to many current monitoring leads in use, such as standard electrocardiogram monitoring leads. The cord 21 is anchored to the block housing the body of the switch device 12 by a plate of insulative material 24 of the same composition as the main body 12, and sealed with suitable adhesives. The mercury ball 22 is then placed in one of the chambers, and the entire upper surface closed by application of the top cover 13 whic is also sealed by adhesives. The final step is to apply a removable adhesive to the bottom surface of the assembly 24 in order to prepare it for use on a patient.

Tests conducted with a series of working models of dimensions, angles and ratios corresponding to those mentioned above have confirmed the operational features described. In particular, there is a notable absence of false alarms due to random movements or turns by the monitored patient, even during chnages of position for nursing care or for meals. However, when the patient does exceed the permitted inclination, either from a supine position or while arising from lying on either side, the switch device is prompt in activating the attached alarm system. Furthermore, once activated, the persistence of electrical contact by the mercury droplet in the foot chamber insures a continuing alarm even if the patient should turn or fall, and requires a prompt response by the attending personnel.

Having fully described my invention, it is to be understood that I am not to be limited to the details herein set forth but that my invention is of the full scope of the appended claims.

I claim:

1. A mercury swtich assembly adapted to be secured to a patient for detecting changes in position, comprising in combination: a body having electrically non-conducting wall surfaces defining a head chamber and a foot chamber spaced by a connecting narrow throat passageway, said chambers being deeper and wider than said throat passageway, spaced electrodes projecting into said foot chamber, a ball of mercury capable of contacting said electrodes to form an electrical connection between them, said ball of mercury having a volume less than the volume of the head chamber and being normally contained within said head chamber when the switch assembly is in normal horizontal position, said walls being so shaped that said ball of mercury moves by gravity without delay from said head chamber through said narrow throat passageway and into said foot chamber when the switch assembly is tilted to incline said throat passageway to a slope of from 40° to 70° from horizontal, said head chamber having lateral extensions of substantial depth for continuously retaining said ball of mercury in said head chamber during lateral turning movement of the switch assembly when the inclination of said throat passageway is less than said slope inclination.

2. The combination set forth in claim 1 in which said slope inclination range is from 50° to 60°.

3. The combination set forth in claim 1 in which said head chamber has a bottom wall surface inclined from 40° to 70° from a bottom wall surface of said narrow throat passageway.

4. The combination set forth in claim 1 in which said head chamber has a bottom wall surface inclined from 50° to 60° from a bottom wall surface of said narrow throat passageway.

5. The combination set forth in claim 1 in which the height of the head chamber is from 5.0 mm to 10.0 mm, the depth is from 3.5 mm to 5.0 mm, and the width is 10.0 mm to 20.0 mm.

6. The combination set forth in claim 1 in which the depth of the foot chamber is from 3.5 mm to 5.0 mm and the width is from 3.0 mm to 7.0 mm.

7. The combination set forth in claim 2 in which said head chamber has a bottom wall surface inclined from 50° to 60° from a bottom wall surface of said narrow throat passageway.

8. A mercury switch assembly adapted to be secured to a patient for detecting changes in position, comprising in combination: a body having electrically non-conducting wall surfaces defining a head chamber and a foot chamber spaced by a connecting throat passageway having a depth of 2.0 mm to 3.5 mm and a width of 3.0 mm to 4.0 mm, said chambers being deeper and wider than said throat passageway, spaced electrodes projecting into said foot chamber, a mercucry ball about 3.5 mm diameter capable of contacting said electrodes to form an electrical connection between them, said mercury ball having a volume less than that of the head chamber and approximately the same as the foot chamber, and being normally contained within said head chamber when the switch assembly is in normal horizontal position, said walls being so shaped that said mercury ball moves by gravity from said head chamber through said throat passageway and into said foot chamber only when the switch assembly is tilted to incline said throat passageway to a predetermined degree, said throat passageway having a smooth rounded intersection with said head chamber and having an abrupt shoulder intersecting said foot chamber, said abrupt shoulder preventing return of said mercury ball to said head chamber until the switch assembly is moved to bring the inclination of said throat passageway to substantially a vertical position, with the foot chamber above the head chamber.

9. The combination set forth in claim 8 in which said head chamber has a bottom wall surface inclined from 50° to 60° from a bottom wall surface of said narrow throat passageway.

10. The combination set forth in claim 8 in which the height of the head chamber is from 5.0 mm to 10.0 mm, the depth is from 3.5 mm to 5.0 mm, and the width is 10.0 mm to 20.0 mm.

11. The combination set forth in claim 8 in which the depth of the foot chamber is from 3.5 mm to 5.0 mm, and the width is from 3.0 mm to 7.0 mm.

12. A mercury switch assembly adapted to be secured to a patient for detecting changes in position, comprising in combination: a body formed of electrically non-conducting material having walls defining a head chamber and a foot chamber longitudinally spaced, the body having a narrow throat passageway connecting said chambers, said chambers being deeper and wider than said throat passageway, spaced electrodes projecting into said foot chamber, a mercury ball capable of contacting said electrodes to form an electrical connection between them, said mercury ball having a volume less than that of the head chamber and approximately the same as the foot chamber and being normally contained within said head chamber when the switch assembly is in normal horizontal position, said walls being so shaped that said mercury ball moves by gravity from said head chamber through said narrow throat passageway and into said foot chamber only when the switch assembly is tilted to incline said throat passageway to a predetermined degree, said throat passageway having a smooth rounded intersection with said head chamber and having an abrupt shoulder intersecting said foot chamber, said abrupt shoulder preventing return of said mercury ball to said head chamber until the switch assembly is moved to bring the inclination of said throat passageway to substantially a vertical position, with the foot chamber above the head chamber, said electrodes each curving about a central axis of the foot chamber, each crossing over to the opposite side thereof while remaining spaced from the other electrode.

* * * * *

UNITED STATES PATENT AND TRADEMARK OFFICE
CERTIFICATE OF CORRECTION

PATENT NO. : 4,348,562
DATED : September 7, 1982
INVENTOR(S) : Robert E. Florin

It is certified that error appears in the above—identified patent and that said Letters Patent is hereby corrected as shown below:

Column 2, line 11, "required" should read --requires--

Column 2, line 30, "interior" should read --inferior--

Column 4, line 15, "type" should read --the--

Column 4, line 42, correct spelling of "which"

Column 4, line 51, correct spelling of "changes"

Signed and Sealed this

Tenth Day of May 1983

[SEAL]

Attest:

Attesting Officer

GERALD J. MOSSINGHOFF

Commissioner of Patents and Trademarks